(12) United States Patent
Anapliotis et al.

(10) Patent No.: US 8,533,968 B2
(45) Date of Patent: Sep. 17, 2013

(54) METHOD AND DEVICE FOR DETERMINING THE COMPATIBILITY BETWEEN AN ADAPTER AND AN OUTER CONE OF A PROSTHESIS SHAFT OF A MODULAR JOINT PROSTHESIS

(75) Inventors: Emmanuel Anapliotis, Berlin (DE); Curt Kranz, Berlin (DE); Martin Hilse, Berlin (DE)

(73) Assignee: Merete Medical GmbH (DE)

( * ) Notice: Subject to any disclaimer, the term of this patent is extended or adjusted under 35 U.S.C. 154(b) by 200 days.

(21) Appl. No.: 13/140,197

(22) PCT Filed: Dec. 11, 2009

(86) PCT No.: PCT/DE2009/001740
§ 371 (c)(1),
(2), (4) Date: Jun. 16, 2011

(87) PCT Pub. No.: WO2010/069292
PCT Pub. Date: Jun. 24, 2010

(65) Prior Publication Data
US 2011/0247229 A1    Oct. 13, 2011

(30) Foreign Application Priority Data
Dec. 18, 2008 (DE) .......................... 10 2008 062 730
Dec. 8, 2009 (DE) .......................... 10 2009 057 117

(51) Int. Cl.
*A61F 2/46* (2006.01)
*A61F 2/30* (2006.01)
*A61F 2/36* (2006.01)

(52) U.S. Cl.
USPC ....... 33/512; 33/501.08; 33/501.45; 33/1 BB; 606/102

(58) Field of Classification Search
USPC ................... 33/512, 501.05, 501.08, 501.45, 33/1 BB, 545, 546, 555.1, 555.3; 606/86 R, 606/102
See application file for complete search history.

(56) References Cited

U.S. PATENT DOCUMENTS 2,330,535 A * 9/1943 Younger .......................... 33/501
4,135,517 A * 1/1979 Reale .......................... 606/86 R
(Continued)

FOREIGN PATENT DOCUMENTS

| DE | 103 29 241 A1 | 2/2005 |
| DE | 103 35 442 A1 | 2/2005 |

(Continued)

OTHER PUBLICATIONS

International Search Report for corresponding application PCT/DE2009/001740, having a mailing date of Jun. 15, 2010.

(Continued)

*Primary Examiner* — Christopher Fulton
(74) *Attorney, Agent, or Firm* — Andrus, Sceales, Starke & Sawall, LLP

(57) ABSTRACT

A method and a device are for determining the compatibility between an adapter, which is to be inserted into a third-party joint ball type to be replaced, and an outer cone of a prosthesis shaft of a modular joint prosthesis, which is inserted in the femur during revision surgery. A test body of a set of test bodies having various inner cones, comprising a marker and a length measuring scale, is fitted onto the outer cone of the shaft of the joint prosthesis and, subsequently, the adapter fitting on the outer cone of the joint prosthesis is determined by successively testing the inner cones for compliance with an admissible minimum distance between the front faces of the outer cone of the shaft of the joint prosthesis and the inner cone and for compliance with an admissible predefined insertion depth of the outer cone of the shaft of the joint prosthesis in the inner cone of the test body.

15 Claims, 6 Drawing Sheets

(56) References Cited

U.S. PATENT DOCUMENTS

| | | | | |
|---|---|---|---|---|
| 4,517,969 A | * | 5/1985 | Halcomb et al. | 606/102 |
| 5,100,407 A | | 3/1992 | Conrad et al. | |
| 5,486,178 A | * | 1/1996 | Hodge | 606/82 |
| 5,562,675 A | * | 10/1996 | McNulty et al. | 606/96 |
| 5,810,831 A | * | 9/1998 | D'Antonio | 606/88 |
| 6,290,704 B1 | * | 9/2001 | Burkinshaw et al. | 606/88 |
| 7,080,461 B2 | * | 7/2006 | Jensen et al. | 33/645 |
| 7,662,156 B2 | * | 2/2010 | Carson | 606/102 |
| 2006/0217815 A1 | | 9/2006 | Gibbs et al. | |
| 2008/0119861 A1 | * | 5/2008 | Winslow et al. | 606/95 |
| 2011/0060339 A1 | * | 3/2011 | de Wekker | 606/80 |

FOREIGN PATENT DOCUMENTS

| | | |
|---|---|---|
| EP | 0 767 638 B1 | 7/1999 |
| WO | 2005/089676 A1 | 9/2005 |

OTHER PUBLICATIONS

Biomet Brochure for Biolox delta Option Ceramic Femoral Head System Product Features and Instructions for Use, Aug. 2012 5 pages.

Zimmer Brochure for Biolox Option Ceramic Femoral Head Data Sheet/Surgical Technique, 2008, 2 pages.

CeramTec Biolox Option System for Revision and Primary Surgery, available at http://www.ceramtec.com/biotox/option/ , last visited Apr. 4, 2013, one page.

Bioceramics and Alternative Bearings in Joint Arthroplasty, 11th Biolox Symposium, Rome, Italy, Jun. 31-Jul. 1, 2006. Proceedings, 18 pages.

McTighe, Timothy et al, "Historical Review of Stem Modularity", Cutting-Edge Developments on Proximal Modularity in THA, Mini-Symposium AAHKS, Dallas, Texas, Nov. 7, 2008, 2 pages.

* cited by examiner

METHOD AND DEVICE FOR DETERMINING THE COMPATIBILITY BETWEEN AN ADAPTER AND AN OUTER CONE OF A PROSTHESIS SHAFT OF A MODULAR JOINT PROSTHESIS

CROSS-REFERENCE TO RELATED APPLICATIONS

This application is the U.S. national stage application of International Application No. PCT/DE2009/001740, filed Dec. 11, 2009, which International application was published on Jun. 24, 2010 as International Publication No. WO 2010/069292 A2 in the German language and which application is incorporated herein by reference. The International applications claims priority of German Patent Application No. 10 2008 062 730.5, filed Dec. 18, 2008, and German Patent Application No. 10 2009 057 117.5, filed Dec. 8, 2009, which applications are incorporated herein by reference.

FIELD

The present disclosure relates to a method for determining the compatibility between an adapter, which is to be inserted into a third-party ball joint provided for replacement, and an outer cone of a prosthesis shaft of a modular joint prosthesis which is inserted into the femur during revision surgery.

The present disclosure further relates to a device for determining the compatibility between an adapter which is to be inserted into a third-party ball joint provided for replacement, and an outer cone of a prosthesis shaft of a modular joint prosthesis which is inserted into the femur during revision surgery.

BACKGROUND

It is known that numerous modular joint prosthesis systems from various manufacturers are in use which result in problems in selecting the correct prosthetic component during the surgical procedure, in particular for the replacement of damaged or worn components of a joint prosthesis, such as ball joints or adapters. Frequently, this is because the manufacturer has discontinued production of the joint prosthesis in question, or the manufacturer is no longer active in the market. During the procedure, the surgeon must quickly decide whether an adapter or a ball joint from a different manufacturer is compatible with the outer cone of the prosthesis shaft which is inserted into the femur, or whether a completely new modular joint prosthesis system must be inserted.

The latter course of action prolongs the procedure for the patient, which is already relatively lengthy, and is often associated with separation of the femur (U.S. Pat. No. 5,100,407 A). In addition, the selection of an adapter which fits on the outer cone of the femoral prosthesis shaft from a set of adapters, using the trial and error method, is time-consuming, and is ultimately unsatisfactory for the patient (EP 0 767 638 B1).

Furthermore, a test instrument is known from DE 103 29 241 A1 for assessing the cone seat of hip endoprostheses, using a test film which allows the bearing area ratio of a cone seat to be determined.

SUMMARY

For this prior art, it is desireable to provide a method and a device for determining the compatibility of an adapter of a joint prosthesis, which make it possible to combine modular components of a joint prosthesis from different manufacturers, to simplify the revision surgery, and to insert ball joints made of ceramic or metal into an already placed shaft, with a precise fit.

According to the present disclosure, the components of modular joint prostheses from different manufacturers are compatible and combinable with one another by using an appropriately matched adapter. This is associated with the great advantage for the patient that the prosthesis shaft which is inserted, into the femur is not removed, and it is necessary only to insert an adapter which is matched to the existing geometric conditions of the outer cone of the prosthesis shaft in order to establish compatibility between the new and the existing components of the prosthesis.

The components of modular joint prostheses from different manufacturers are combined by determining, the compatibility between an inner cone of an adapter and an outer cone of the shaft of a joint prosthesis, wherein a visually observable test piece in the form of a set of test pieces having different inner cones, and having a marker and length measuring scale, is successively placed on the shaft of the joint prosthesis, and the adapter which fits on the shaft of the joint prosthesis is subsequently determined by testing the inner cones for compliance with a minimum permissible distance between the end face of the outer cone of the shaft of the joint prosthesis and the inner cone, and for compliance with a predefined permissible insertion depth of the outer cone of the joint prosthesis into the inner cone of the test piece.

This ensures that during the surgical procedure, the surgeon is able to reliably select the adapter suitable for insertion on the basis of the geometric conditions that are actually present at the outer cone of the shaft of the joint prosthesis, according to the following substeps:

a) Determining the actual distance between the end face of the outer cone of the shaft of the joint prosthesis and the top of the inner cone of the test piece, b) Comparing the actual distance according to step a) to the marker on the test piece as a measure for the minimum permissible distance between the end face of the outer cone of the shaft of the joint prosthesis and the top of the inner cone of the test piece, c) Pulling off the mounted test piece from the outer cone of the shaft of the joint prosthesis as soon as it is determined in step b) that the distance is less than the permissible distance, and mounting another test piece, having a different inner cone, from the set of test pieces, d) Continuing steps a) through c) until the distance actually determined exactly matches or exceeds the marker, e) Assessing the rotational resistance and the tilting tendency by rotating the test piece on the outer cone and identifying a perceivable sliding friction resistance without a tendency to tilt.

f) Determining the actual insertion depth of the outer cone of the shaft of the joint prosthesis into the inner cone of the test piece as a measure for the secure seating of the inner cone on the outer cone of the shaft of the joint prosthesis by reading the length measuring scale on the test piece.

g) Rejecting the selected inner cone of the test piece as soon as it is determined in step f) that the actual insertion depth is less than the minimum permissible insertion depth, and pulling off the test piece, h) Mounting another test piece and continuing steps a) through d) until the insertion depth actually determined is greater than the minimum permissible insertion depth while complying with the minimum permissible distance.

i) Selecting an adapter in reserve supply which has the inner cone determined according to step h), for insertion into the ball joint.

It is also particularly advantageous that the measure for the minimum permissible distance is determined from the tolerances of the corresponding diameter and angle of the inner cone of the test piece and of the outer cone of the shaft of the joint prosthesis, so that geometrically unsuitable adapters ma be reliably and quickly rejected, and wobbling and rotation of the adapter on the outer cone of the shaft of the joint prosthesis may be prevented.

It has been shown that the measure for the minimum permissible insertion depth of the outer cone of the shaft of the joint prosthesis into the inner cone of the test piece is a function of the length of the overlap of the two cones, and that it is sufficient when the insertion depth is at least 7 mm. Test pieces in the form of an incised spherical segment or a cylinder may be used.

The device has a simple and uncomplicated design which is particularly suited for rapidly and reliably determining the correct adapter.

The device includes a set of test pieces, each having, different inner cones, a marker being provided for determining the minimum permissible distance between an end face of the outer cone of the shaft of the joint prosthesis and a top of the inner cone of the test piece close to the top at a cutting edge of the inner cone, and a length measuring scale being situated at the cutting edge of the inner cone for determining the insertion depth of the outer cone of the shaft into the inner cone of the particular test piece.

Using these two measuring means, during, the surgical procedure the surgeon is able to quickly visually determine the minimum permissible distance between the end face of the outer cone of the shaft of the joint prosthesis and the insertion depth of the outer cone of the shaft into the inner cone of the test piece, and to immediately decide whether the selected inner cone is a suitable match.

The test piece may have the shape of a spherical segment or an incised cylinder which is visually observable from the outside.

Further advantages and particulars result from the following description, with reference to the accompanying drawings.

BRIEF DESCRIPTION OF THE DRAWINGS

The present disclosure is explained in greater detail below.

FIG. 1 shows the basic design of the device according to the present disclosure for determining the compatibility between an adapter which is to be inserted into a third-party ball joint provided for replacement, and an outer cone of a prosthesis shaft of a modular joint prosthesis which is inserted into the femur.

Figure 1:
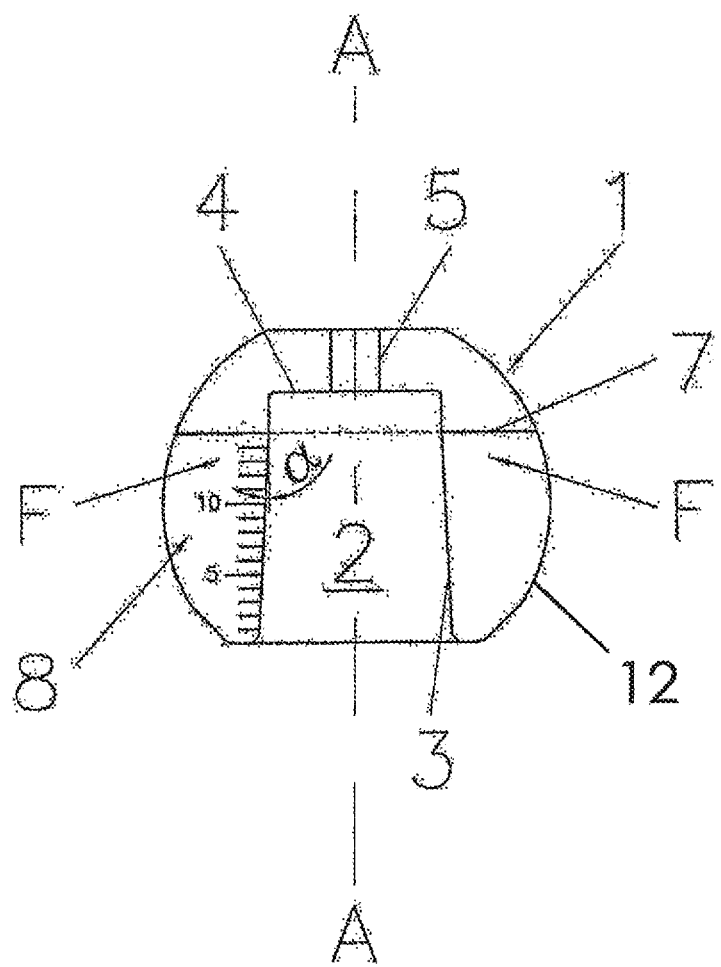
FIG. 1 shows a front view of the test piece of the device, in the form of an incised spherical segment having a marker for determining the minimum permissible distance, and a length measuring scale for determining the insertion depth.

The device includes at least one test piece 1 having a measuring area 2 which is delimited by an inner cone 3 that is open at its lateral surface area, and a top 4. The top 4 forms the upper end of the measuring area 2. A borehole 5 which leads into the measuring area 2 is centrally provided in the top 4, and is used for receiving or inserting a separating, instrument, not described here in greater detail. The test piece 1 may have a spherical segmented design (see FIGS. 1 through 4), or also a cylindrical design.

Figure 2:
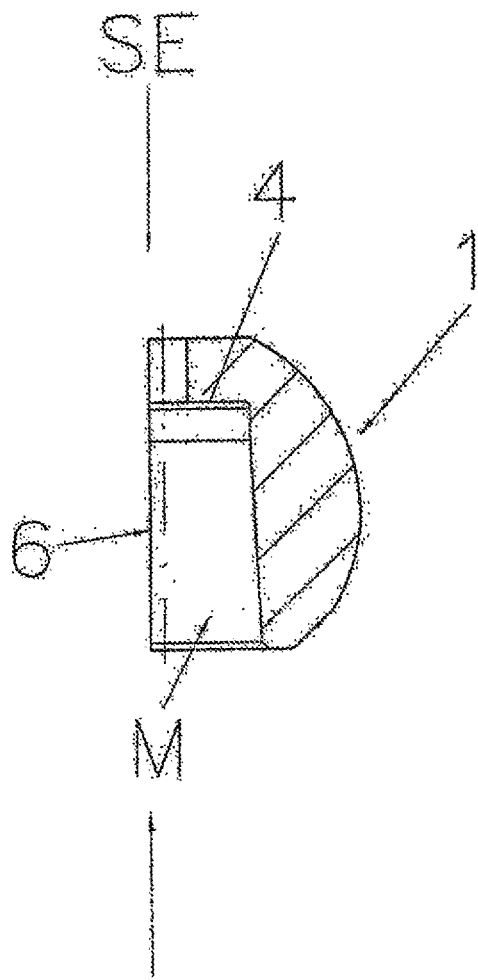
FIG. 2 shows a side view according to FIG. 1.

The inner cone 2 has an opening 6 in its shell M which originates from a cross section along a plane SE of the spherical segmented test piece 1, so that the opening 6 is delimited by surfaces F extending, parallel to axis A of the test piece 1 (see FIG. 2). A marker 7 and a length measuring scale 8 are introduced into these surfaces F near the top 4, the marker 7 at the same time being the starting point of the length measuring scale 8. The opening 6 is positioned in such a way that the marker 7 as well as the length measuring scale 8 are readable by the surgeon, and the end face 9 of the outer cone 10 of the shaft 11 of the joint prosthesis is identifiable.

The device includes at least one set of test pieces 1 having different cone angles $\alpha$ and diameters which are graduated from one test piece to the next.

Figure 3:
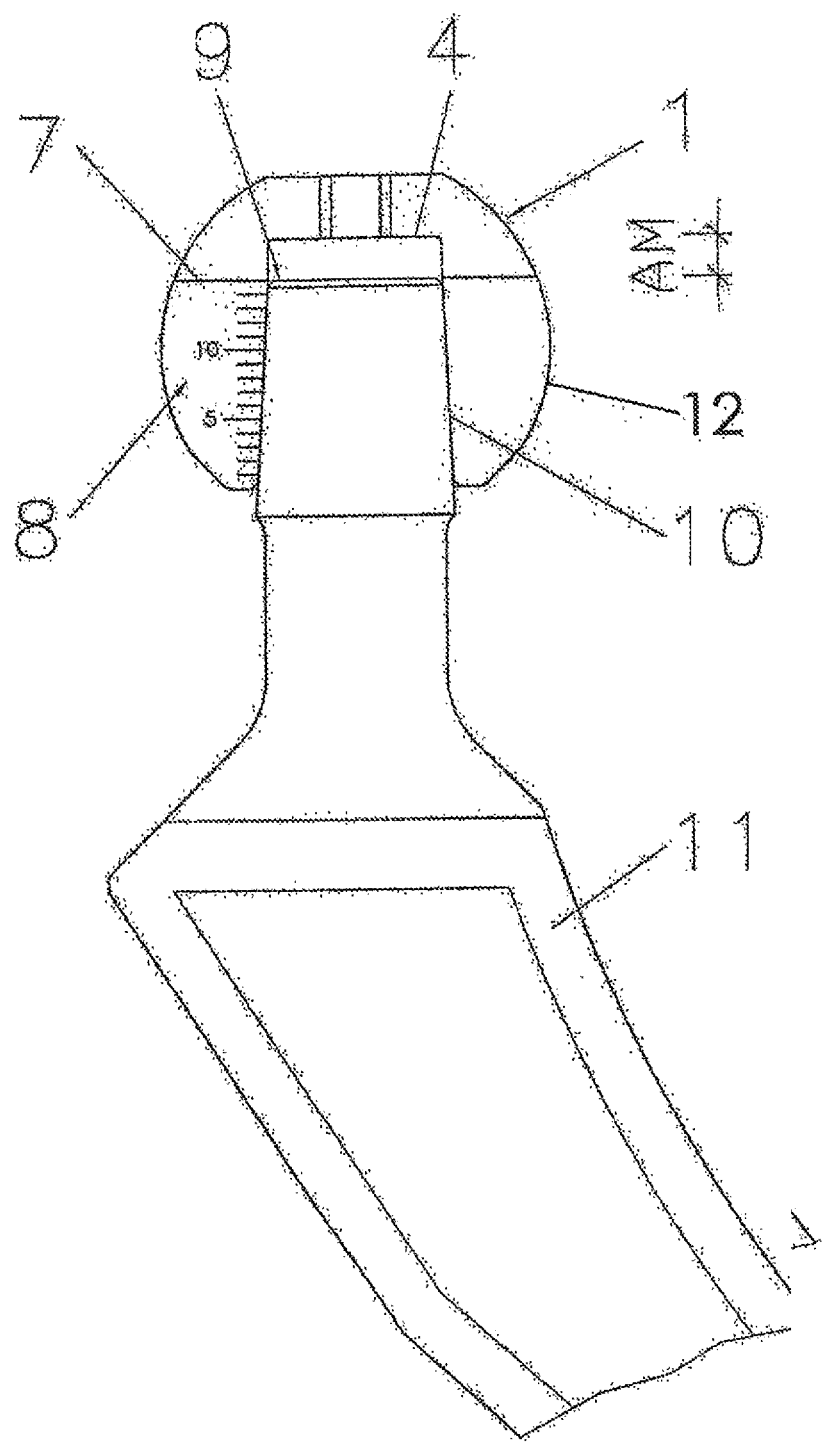
FIG. 3 shows a schematic view of the device, having a spherical segment in the mounted state on the outer cone of the shaft of the joint prosthesis, for determining the minimum permissible distance.

FIG. 3 shows the test piece 1 in the mounted state on the outer cone 10 of a shall 11 of a joint prosthesis for determining the distance AM between the end face 9 of the outer cone 10 and the top 4 of the test piece 1. In the example shown, the marker 7 almost coincides with the position of the end face 9 of the outer cone 10 of the shaft 11 of the joint prosthesis. The position of the marker 7 on the surface F, which is different for each test piece 1, results from the known tolerances of the corresponding diameter and angle of the inner cone 3 of the test piece 1 and of the outer cone 10 of the shaft 11 of the joint prosthesis, as well as from a safety factor to be specified. Compliance with the minimum permissible distance AM is obtained when the position of the marker 7 matches the end face 9 of the outer cone 10. If the distance AM is too small, the surfaces may become superposed, so that wobbling, rotation, and wear can no longer be ruled out. Thus, when the marker 7 and the position of the end face 9 do not match, this indicates that the distance AM is too small, and therefore the selected inner cone 3 is rejected.

Figure 4:
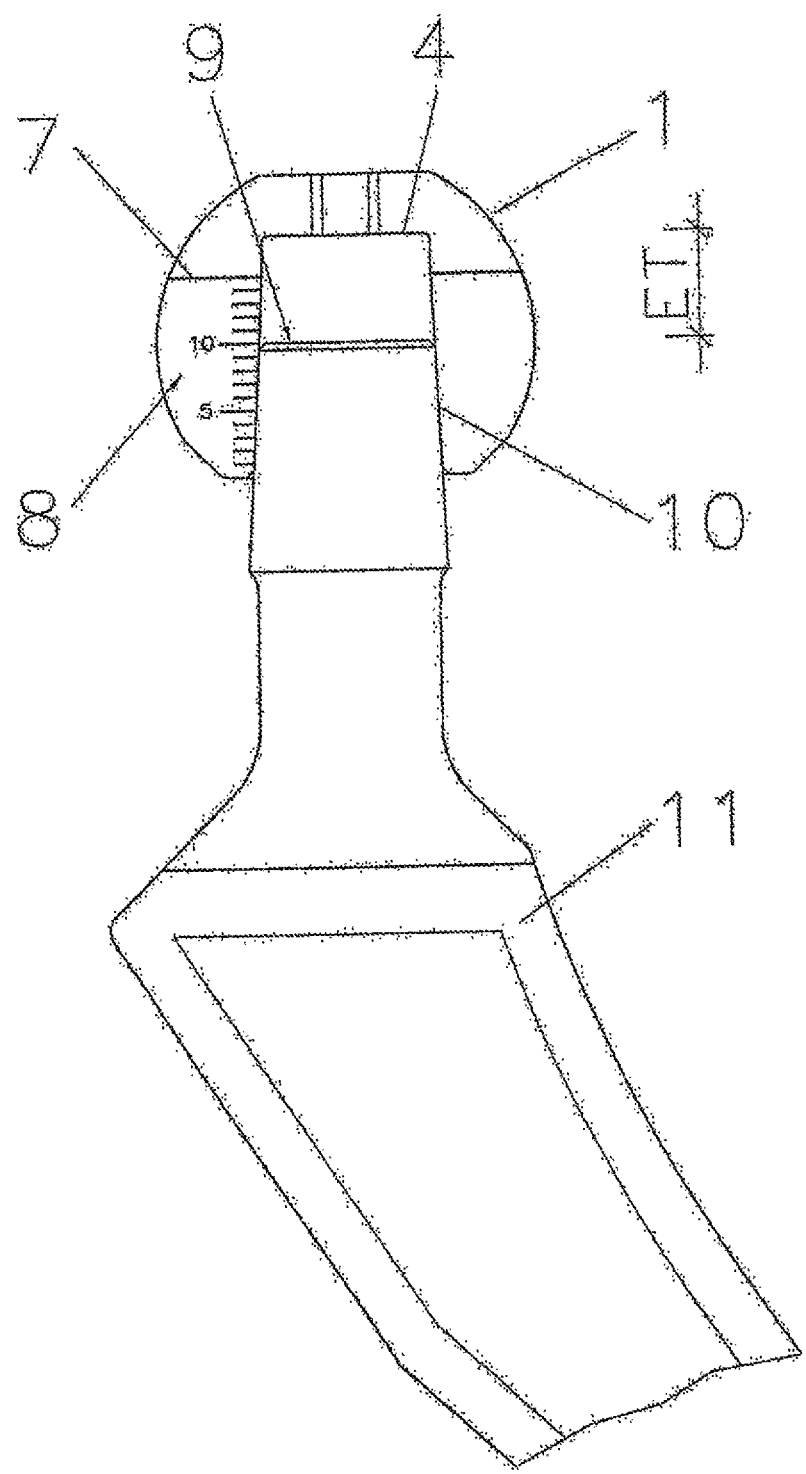
FIG. 4 shows a schematic [view] of the device, having a spherical segment in the mounted state on the outer cone of the shaft of the joint prosthesis, for determining the insertion depth.

FIG. 4 shows the determination of the insertion depth ET of the outer cone 10 into the inner cone 3 of the test piece 1. The insertion depth ET specifies the secure hold of the inner cone 3 on the outer cone 10, and is essentially a function of the length of the overlap of the two cone surfaces.

It has been shown that a secure hold is ensured when the insertion depth ET is at least 7 mm.

Figure 5:
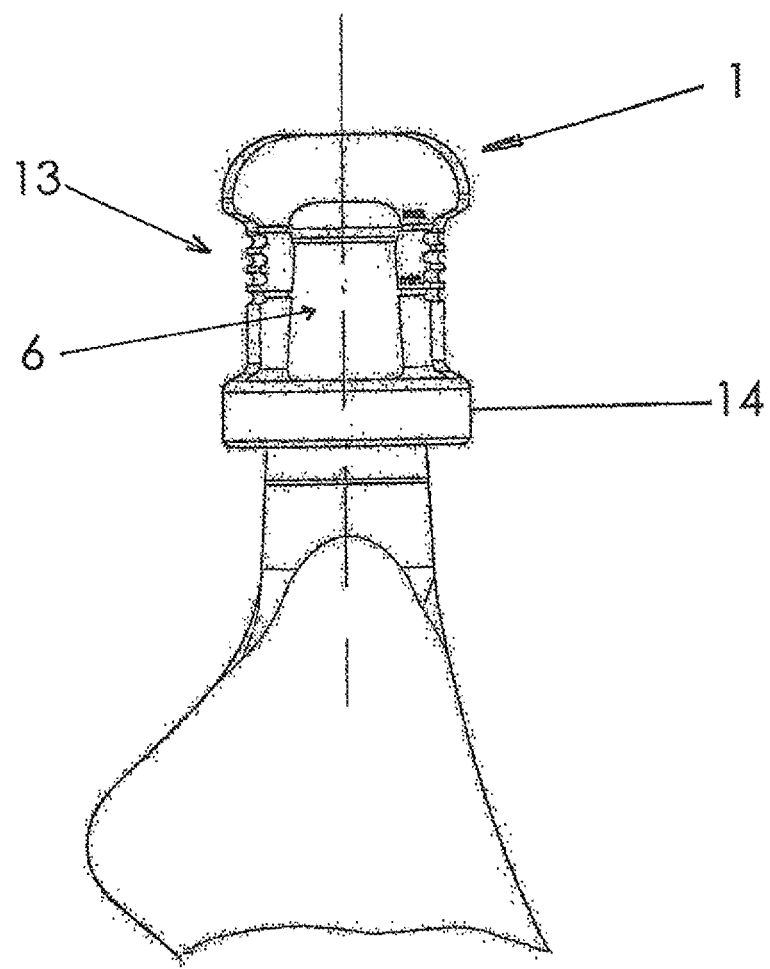
FIG. 5 shows a schematic view of the test piece of the device, in the form of an incised cylinder.

FIG. 5 shows a variant of the test piece 1, in the form of an incised cylinder 13 which is provided, with a circumferential collar 14 beneath its opening 6. The opening 6 in the shell M of the test piece 1 basically corresponds to the design described in paragraph with respect to FIG. 1. In the present case, the length measuring scale 8 has markers for minimum and maximum reading points.

Figure 6:
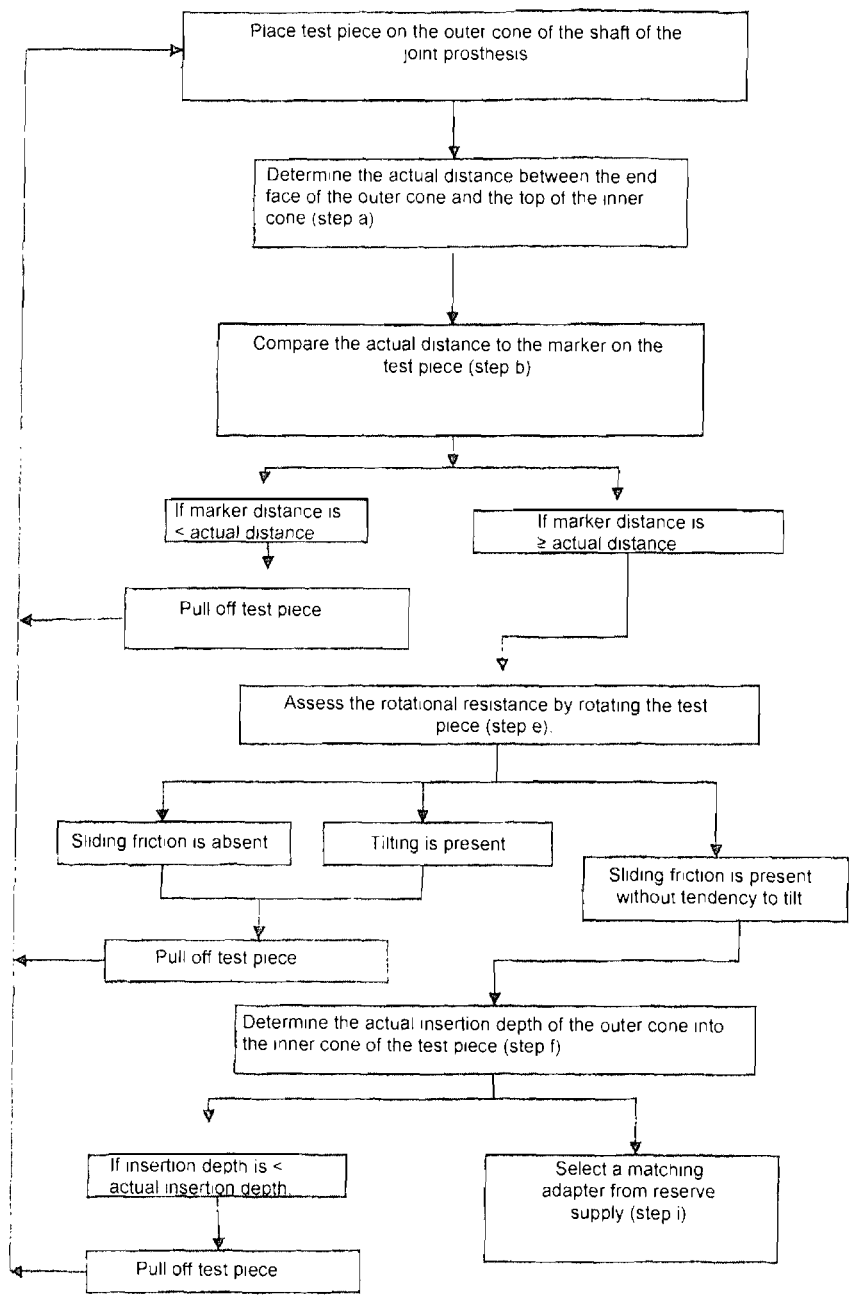
FIG. 6 shows a schematic illustration of the sequence of the method.

FIG. 6 schematically shows the sequence of the method.

The test piece 1 of a set of test pieces, each having a different inner cone 2, is placed on the outer cone 10 of the shaft 10 of the joint prosthesis, and the actual distance AM between the end face 9 of the outer cone 10 and the top 4 of the inner cone 3 is determined (step a). For this purpose, the position of the end face 9 is compared to the marker 7 on the surface F of the test piece 1. If the comparison shows that this value is less than distance AM, the test piece 1 is pulled off the outer cone 10 of the shaft 11 and a new test piece 1, for example having a larger cone diameter D or a larger cone angle α, is selected from the set of test pieces. This new test piece 1 is then once again placed on the outer cone 10 of the shaft 11 of the joint prosthesis, and the distance AM is determined. If it is determined that the actual distance is equal to or greater than distance AM, the rotational resistance and the tilting tendency of the test piece 1 on the outer cone 10 of the shaft 11 are assessed (step e) by rotating the test piece 1 on the outer cone 10. If no tilting, tendency is identified, and a perceivable sliding friction during rotation may be overcome, the actual insertion depth ET of the outer cone 10 of the shaft 11 into the inner cone 3 of the test piece 1 is determined (step f). If there is no perceivable sliding friction without a tendency to tilt, the test piece 1 is pulled off and a new test piece 1, once again having a different cone diameter D and cone angle α, from the set of test pieces is placed on the outer cone 10. The test procedure begins anew with step a).

If during the determination of the insertion depth ET it is found that the actual insertion depth exceeds a minimum permissible insertion depth which is specified as a function of the cone length, the conditions for compatibility of the inner cone 3 with the present test piece, which must be complied with for the selection, are met, and the appropriately matching adapter for the joint component may be selected from a reserve supply provided for this purpose.

The execution of the invention is not limited to the exemplary embodiments described above. Rather, variants are conceivable which may depart from the described approach, even for basically different executions.

The invention claimed is:

1. A method for determining the compatibility between an adapter, which is to be inserted into a third-party ball joint provided for replacement, and an outer cone of a prosthesis shaft of a modular joint prosthesis which is inserted into the femur during revision surgery, wherein a test piece of a set of test pieces having different inner cones, and having a marker and a length measuring scale, is placed on the outer cone of the shall of the joint prosthesis, and the adapter which fits on the outer cone of the joint prosthesis is subsequently determined by successively testing the inner cones for compliance with a minimum permissible distance between the end faces of the outer cone of the shaft of the joint prosthesis and the inner cone, and for compliance with a predefined permissible insertion depth of the outer cone of the shaft of the joint prosthesis into the inner cone of the test piece.

2. The method according to claim 1, wherein the following substeps are carried out:
   a) determining the actual distance between the end face of the conical shaft of the joint prosthesis and the top of the inner cone of the test piece,
   b) comparing the actual distance according to step a) to a marker on the test piece as a measure for the minimum permissible distance between the end face of the outer cone of the shaft of the joint prosthesis and the top of the inner cone of the test piece,
   c) pulling off the mounted test piece from the outer cone of the shall of the joint prosthesis as soon as it is determined in step h) that the distance is less than the permissible distance, and mounting another test piece, having a different inner cone, from the set of test pieces,
   d) continuing steps a) through c) until the distance actually determined exactly matches or exceeds the marker,
   e) assessing the rotational resistance and the tilting tendency by rotating the test piece on the outer cone and identifying a perceivable sliding friction resistance without a tendency to tilt,
   f) determining the actual insertion depth of the outer cone of the shaft of the joint prosthesis into the inner cone of the test piece as a measure for the secure seating of the inner cone on the outer cone of the shaft of the joint prosthesis by reading the length measuring scale on the test piece,
   g) rejecting the selected inner cone of the test piece as soon as it is determined in step f) that the actual insertion depth is less than the permissible insertion depth, and pulling off the test piece,
   h) mounting another test piece having a different diameter and angle, and continuing steps a) through d) until the insertion depth actually determined is greater than the permissible insertion depth while complying with the minimum permissible distance, and
   i) selecting an adapter in reserve supply which has the inner cone determined according to step h), for insertion into the ball joint.

3. The method according to claim 1, wherein the measure for the minimum permissible distance is determined from the tolerances of the corresponding diameter and angle of the inner cone of the test piece and of the outer cone of the shaft of the joint prosthesis.

4. The method according to claim 1, wherein the measure for the permissible insertion depth of the outer cone of the shaft of the joint prosthesis into the inner cone of the lest piece is determined according to the length of the inner cone of the test piece.

5. The method according to claim 1, wherein the permissible insertion depth is set to be at least 7 mm.

6. A method according to claim 1, wherein an incised molded body, for example in the shape of a spherical segment or cylindrical segment, is used as the test piece.

7. A device for determining the compatibility between an adapter which is to be inserted into a third-party ball joint provided for replacement, and an outer cone of a prosthesis shaft of a modular joint prosthesis which is inserted into the femur during revision surgery, for carrying out the method according to claim 1, wherein the device includes a set of test pieces in the form of incised spherical or cylindrical segments, each having a different inner cone, wherein a marker for determining the minimum permissible distance between an end face of the outer cone of the shaft of the joint prosthesis and a top of the inner cone of the test piece close to the top is provided on a surface of the inner cone, and a length measuring scale for determining the insertion depth of the outer cone of the shaft into the inner cone of the particular test piece is situated on the surface of the inner cone.

8. The device according to claim 7, wherein the inner cones of the test pieces of the set of test pieces have different angles and diameters.

9. The device according to claim 7, wherein the minimum permissible distance takes into account tolerances of the corresponding diameter and angle of the inner cone of the test piece and of the outer cone of the shaft of the joint prosthesis.

10. The device according to claim 9, wherein the permissible insertion depth is at least 7 mm.

11. The device according to claim 7, wherein the permissible insertion depth of the outer cone of the shaft into the inner cone of the test piece is matched to the length of the inner cone of the test piece.

12. The device according to claim 7, wherein a set of adapters for inserting or adapting the ball joint is associated with the set of test pieces.

13. The device according to claim 7, wherein the cylindrical segment has a circumferential collar beneath its opening for securely placing the test piece on the outer cone of the shaft.

14. A method for determining the compatibility between a component and an outer cone of a prosthesis shaft of a modular joint prosthesis which is inserted into the femur during revision surgery, the method comprising placing a test piece of a set of test pieces having different inner cones, and having a marker and a length measuring scale, on the outer cone of the shaft of the joint prosthesis, and subsequently determining the component which fits on the outer cone of the joint prosthesis by successively testing the inner cones for compliance with a minimum permissible distance between the end faces of the outer cone of the shaft of the joint prosthesis and the inner cone, and for compliance with a predefined permissible insertion depth of the outer cone of the shaft of the joint prosthesis into the inner cone of the test piece.

15. A device for determining the compatibility between a component and an outer cone of a prosthesis shaft of a modular joint prosthesis which is inserted into the femur during revision surgery, wherein a test piece of a set of test pieces having different inner cones, and having a marker and a length measuring scale, is placed on the outer cone of the shaft of the joint prosthesis, and the component which fits on the outer cone of the joint prosthesis is subsequently determined by successively testing the inner cones for compliance with a minimum permissible distance between the end faces of the outer cone of the shaft of the joint prosthesis and the inner cone, and for compliance with a predefined permissible insertion depth of the outer cone of the shaft of the joint prosthesis into the inner cone of the test piece, the device comprising:

the set of test pieces in the form of incised spherical or cylindrical segments, each having a different inner cone, wherein the marker for determining a minimum permissible distance between an end face of the outer cone of the shaft of the joint prosthesis and a top of the inner cone of the test piece close to the top is provided on a surface of the inner cone, and the length measuring scale for determining the insertion depth of the outer cone of the shaft into the inner cone of the particular test piece is situated on the surface of the inner cone.

* * * * *